(12) United States Patent
Nguyen et al.

(10) Patent No.: US 9,050,077 B2
(45) Date of Patent: Jun. 9, 2015

(54) SUTURE ANCHOR INSERTER

(75) Inventors: Linh Nguyen, Randolph, MA (US);
Julie Tripodi, Marlborough, MA (US)

(73) Assignee: Smith & Nephew, Inc., Memphis, TN (US)

( * ) Notice: Subject to any disclaimer, the term of this patent is extended or adjusted under 35 U.S.C. 154(b) by 590 days.

(21) Appl. No.: 12/212,932

(22) Filed: Sep. 18, 2008

(65) Prior Publication Data
US 2010/0069923 A1    Mar. 18, 2010

(51) Int. Cl.
*A61B 17/10* (2006.01)
*A61B 17/04* (2006.01)
*A61B 17/06* (2006.01)

(52) U.S. Cl.
CPC ..... *A61B 17/0401* (2013.01); *A61B 2017/0409* (2013.01); *A61B 2017/0414* (2013.01); *A61B 2017/044* (2013.01); *A61B 2017/06057* (2013.01)

(58) Field of Classification Search
CPC .................. A61B 17/0401; A61B 2017/0409; A61B 2017/0414; A61B 2017/044; A61B 2017/06057
USPC .............................. 606/72–74, 232–233, 139
See application file for complete search history.

(56) References Cited

U.S. PATENT DOCUMENTS

| | | | | |
|---|---|---|---|---|
| 4,285,255 A * | 8/1981 | Winfrey | .......................... | 81/451 |
| 5,827,291 A * | 10/1998 | Fucci et al. | ................... | 606/104 |
| 5,849,004 A | 12/1998 | Bramlet | | |
| 5,897,574 A | 4/1999 | Bonutti | | |
| 5,944,724 A | 8/1999 | Lizardi | | |
| 5,944,739 A | 8/1999 | Zlock et al. | | |
| 6,102,934 A * | 8/2000 | Li | ................................ | 606/232 |
| 6,660,022 B1 * | 12/2003 | Li et al. | ......................... | 606/232 |
| 6,951,565 B2 | 10/2005 | Keane et al. | | |
| 7,645,293 B2 * | 1/2010 | Martinek et al. | .............. | 606/232 |
| 2003/0204195 A1 | 10/2003 | Keane et al. | | |
| 2004/0106935 A1 | 6/2004 | Merves | | |
| 2005/0240199 A1 | 10/2005 | Martinek et al. | | |

FOREIGN PATENT DOCUMENTS

| | | |
|---|---|---|
| EP | 0611551 A1 | 2/1994 |
| EP | 0838197 A2 | 4/1998 |
| EP | 1588666 A2 | 10/2005 |
| JP | 2002516585 A | 6/2002 |
| WO | 99/22648 | 5/1999 |
| WO | 99/62410 | 12/1999 |
| WO | 03/090627 A2 | 11/2003 |
| WO | 03/090629 A2 | 11/2003 |
| WO | 2006/110530 A2 | 10/2006 |

OTHER PUBLICATIONS

International Search Report and Written Opinion for PCT/US2009/054128 Dated Nov. 13, 2009.
Notice of Reason for Rejection for Japanese Application No. 2011-527860, mailed Aug. 4, 2014.
First Examination Report for Australian patent application 2009293562, mailing date Oct. 2, 2014.
Notice of Reason for Rejection for Chinese Application No.: 2009-80136675.6, mailed Mar. 2, 2015.

* cited by examiner

*Primary Examiner* — Gregory Anderson
(74) *Attorney, Agent, or Firm* — Burns & Levinson LLP; Joseph M. Maraia

(57) ABSTRACT

The present disclosure relates to a suture anchor inserter. The suture anchor inserter includes a handle having a proximal component, a central component coupled to the proximal component, and a distal component coupled to the proximal component and the central component, the central component capable of rotating relative to the proximal component; and a shaft comprising a proximal end and a distal end, the proximal end coupled to the handle. A method of inserting a suture anchor into bone is also disclosed.

23 Claims, 13 Drawing Sheets

SUTURE ANCHOR INSERTER

BACKGROUND

1. Field of Technology

The present disclosure relates to the surgical repair of tissue and, more specifically, devices and methods for the insertion of a suture anchor used in such repair.

2. Related Art

Suture anchors are commonly used to attach soft and hard tissue to bone. Typically, a suture anchor is implanted into a drilled bore in bone mass. One or more sutures with attached needles are connected to the suture anchor. The suture is passed through the tissue and subsequently tied to secure the tissue to the bone. A device for placement of the suture anchor is needed that both stores the suture and needles and allows for them to be deployed easily by the user. In addition, the device must provide tension on the suture so that the anchor remains engaged with the device.

SUMMARY OF THE INVENTION

In one aspect, the present disclosure relates to a suture anchor inserter. The suture anchor inserter includes a handle having a proximal component, a central component coupled to the proximal component, and a distal component coupled to the proximal component and the central component, the central component capable of rotating relative to the proximal component; and a shaft comprising a proximal end and a distal end, the proximal end coupled to the handle. In an embodiment, the suture anchor inserter further includes the suture anchor coupled to the distal end of the shaft.

In another embodiment, the proximal component further includes at least two holes. In yet another embodiment, the central component further includes a top surface and a bottom surface, the top surface and the bottom surface both having a groove. In a further embodiment, the distal component further includes a front portion and a back portion, the front portion having at least two suture retainers. In yet a further embodiment, the shaft further includes at least two channels, each channel housing one of the at least two suture retainers. In an embodiment, the suture includes at least two ends, the ends including a needle coupled to each end, the needles housed within the holes. In another embodiment, the suture comprises at least two ends, the ends housed within the grooves of the central component. In yet another embodiment, the suture comprises at least two ends, the ends housed within the channels and retained therein by the suture retainers. In a further embodiment, the proximal portion further includes at least two slots with each slot having a first crevice and a second crevice. In an even further embodiment, the central component further comprises at least two tabs, the two tabs disposed within the first crevice of each slot.

In another aspect, the present disclosure relates to a method of inserting a suture anchor into bone. The method includes providing a suture anchor inserter having a handle including a component capable of rotation, a shaft coupled to the handle, and the suture anchor coupled to the shaft; inserting the suture anchor into bone; rotating the component; and removing the inserter. In an embodiment, the suture comprises at least two ends, the ends comprising a needle coupled to each end, the needles housed within the handle. In another embodiment, rotation of the component allows for release of the suture and the needles from the handle. In yet another embodiment, the handle further includes a component located proximal to the rotatable component, the component including at least two slots with each slot having a first crevice and a second crevice. In a further embodiment, the rotatable component further includes at least two tabs, the two tabs disposed within the first crevice of each slot prior to rotation of the rotatable component and disposed within the second crevice of each slot after rotation of the rotatable component.

In yet another aspect, the present disclosure relates to a suture anchor inserter. The suture anchor inserter includes a handle having a component capable of rotation and a shaft coupled to the handle. In an embodiment, the suture anchor inserter further includes a suture anchor coupled to the ends.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
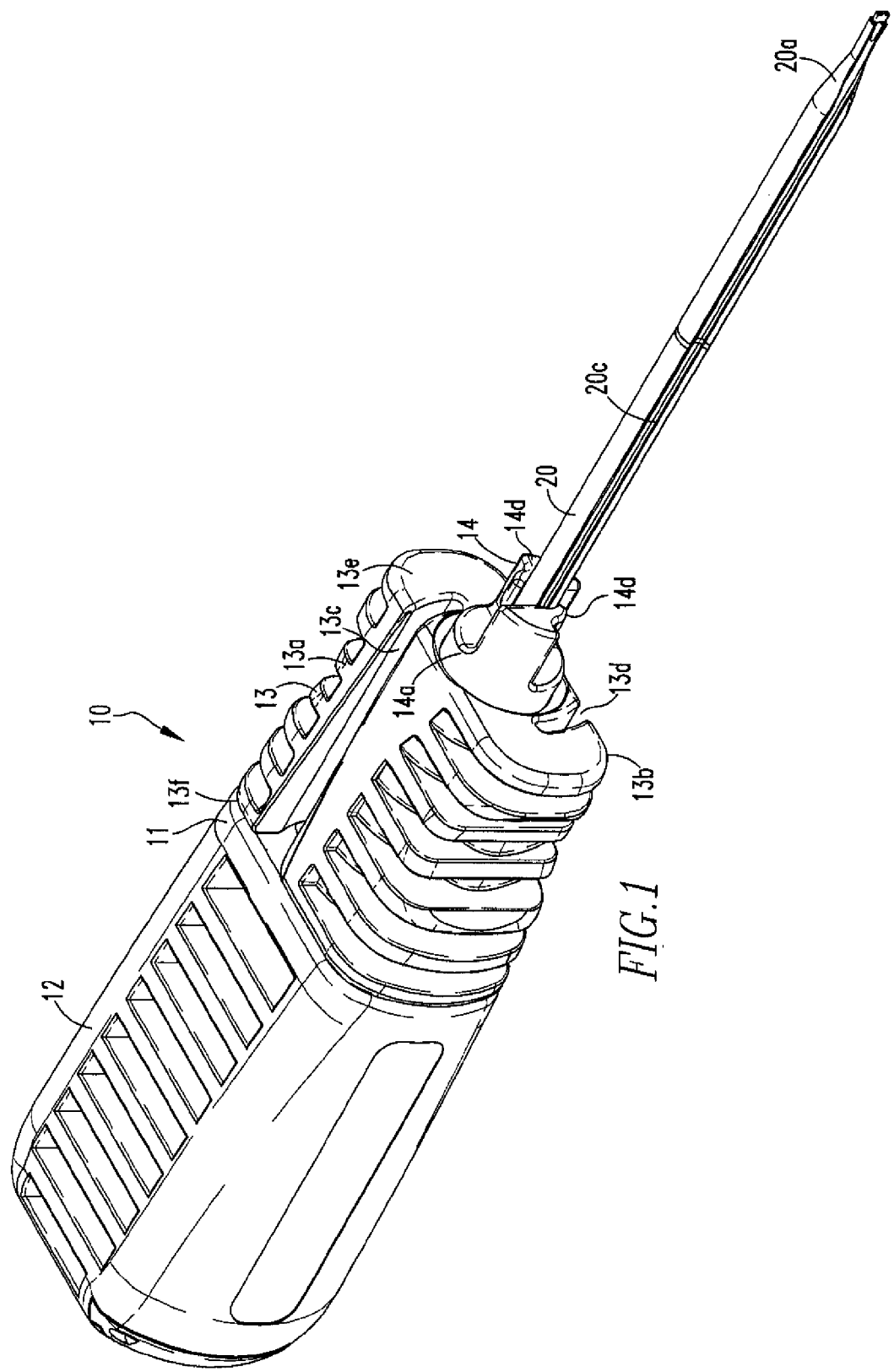
FIG. 1 shows a perspective view of the suture anchor inserter of the present disclosure.
Figure 2:
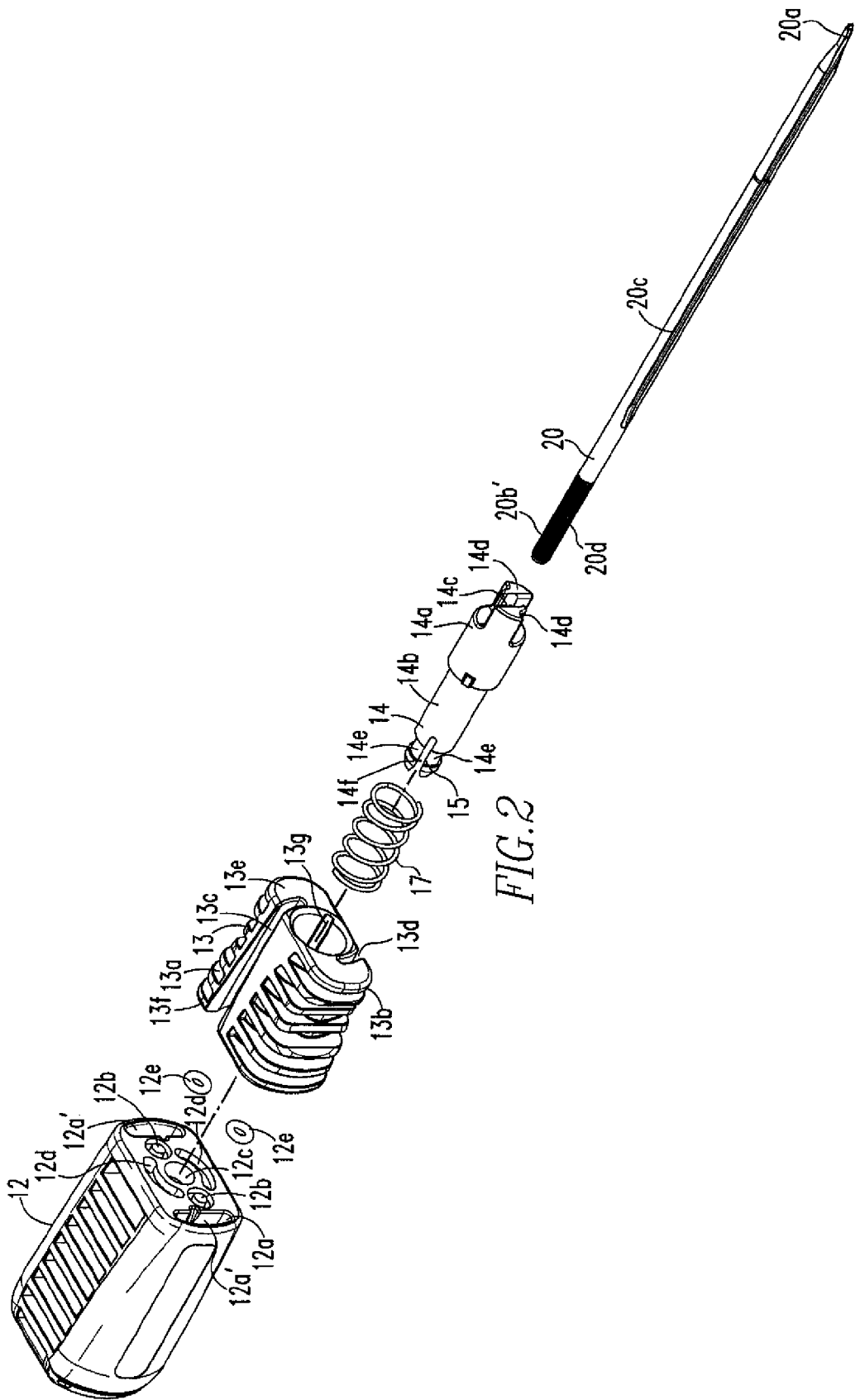
FIG. 2 shows an expanded view of the suture anchor inserter of FIG. 1.
Figure 3:
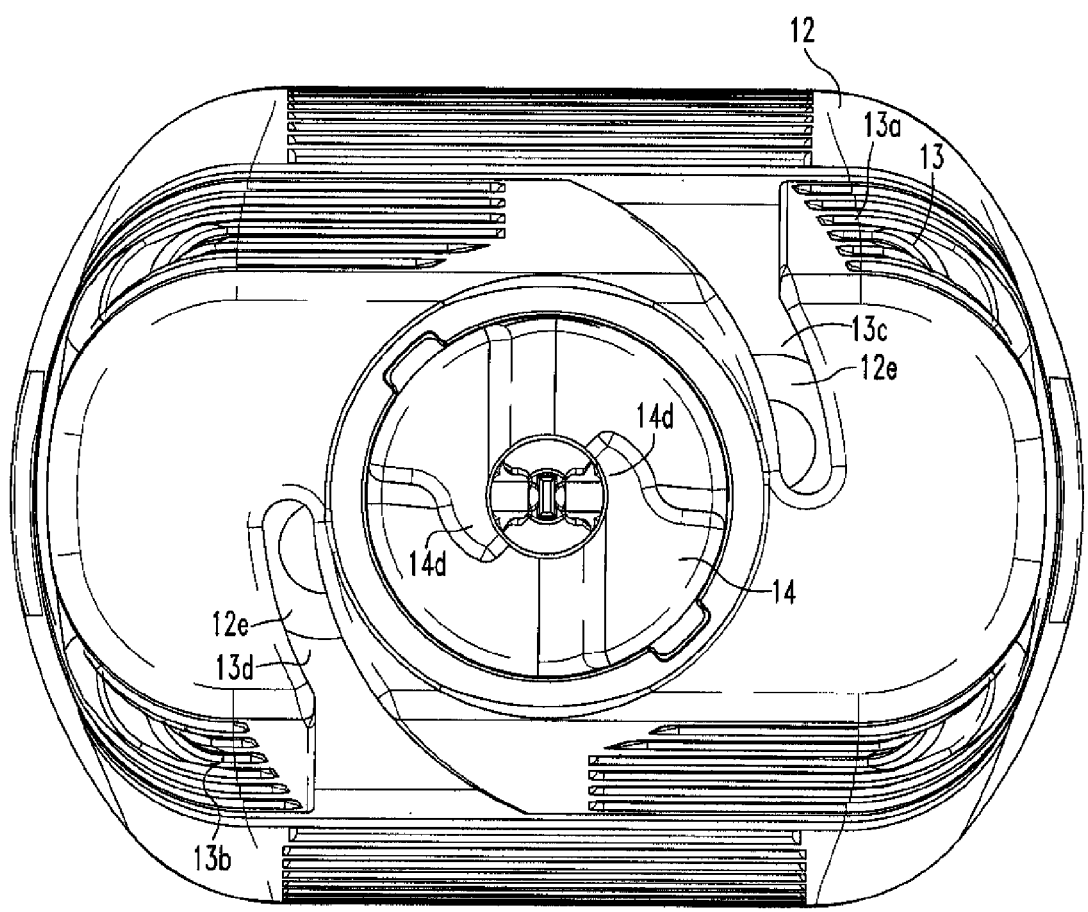
FIG. 3 shows a front view of the suture anchor inserter of FIG. 1.
Figure 4:
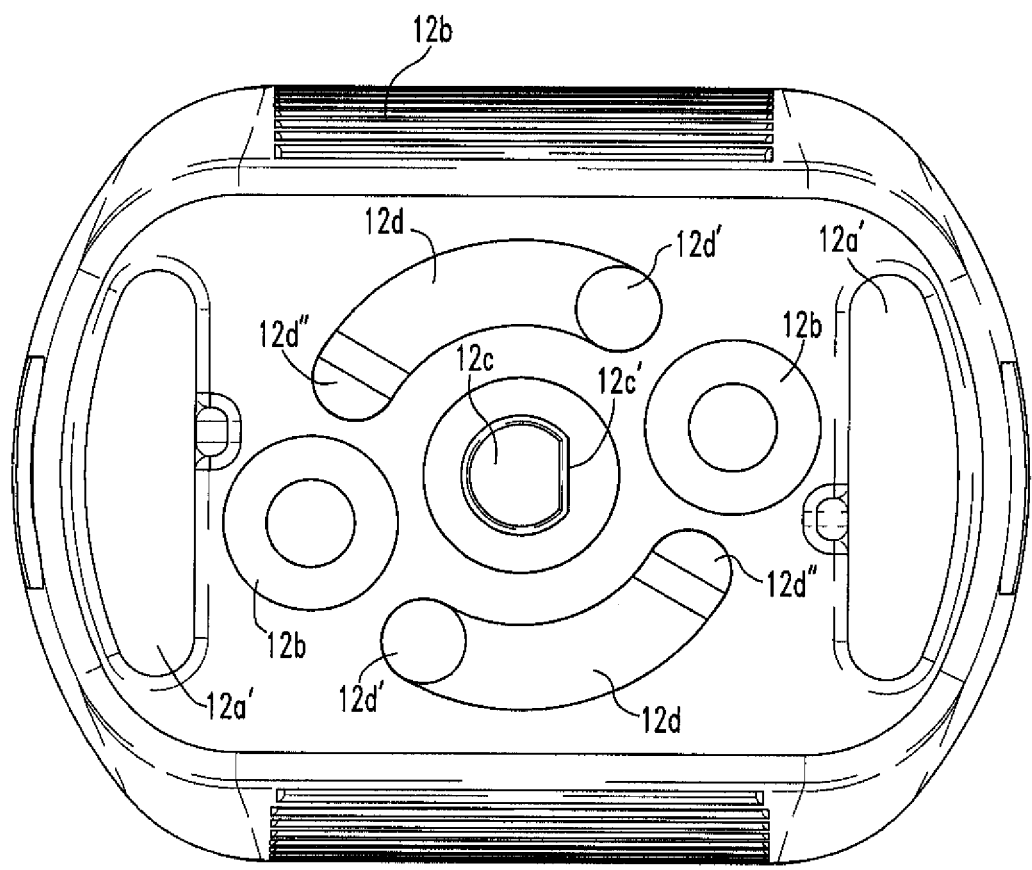
FIG. 4 shows a front view of the proximal component of the suture anchor inserter of FIG. 1.

FIGS. 1-3 show the suture anchor inserter 10 of the present disclosure. The inserter 10 includes a handle 11 and a shaft 20 coupled to the handle 11. The handle 11 includes a proximal component 12, a central component 13, and a distal component 14. The proximal component 12 includes two holes 12a having openings 12a', two depressions 12b located between the holes 12a, an opening 12c located between the depressions 12b, and two slots 12d located above and below the opening 12c. O-rings 12e may be housed within the depressions 12b to substantially reduce the possibility of damage to suture that extends between the proximal component 12 and the central component 13, especially when the central component 13 is rotated, as will be further described below. As shown in FIG. 4, the slots 12d include a first crevice 12d' and a second crevice 12d" at both ends of the slots 12d for housing of tabs on the central component 13, as will be further described below.

Figure 5:
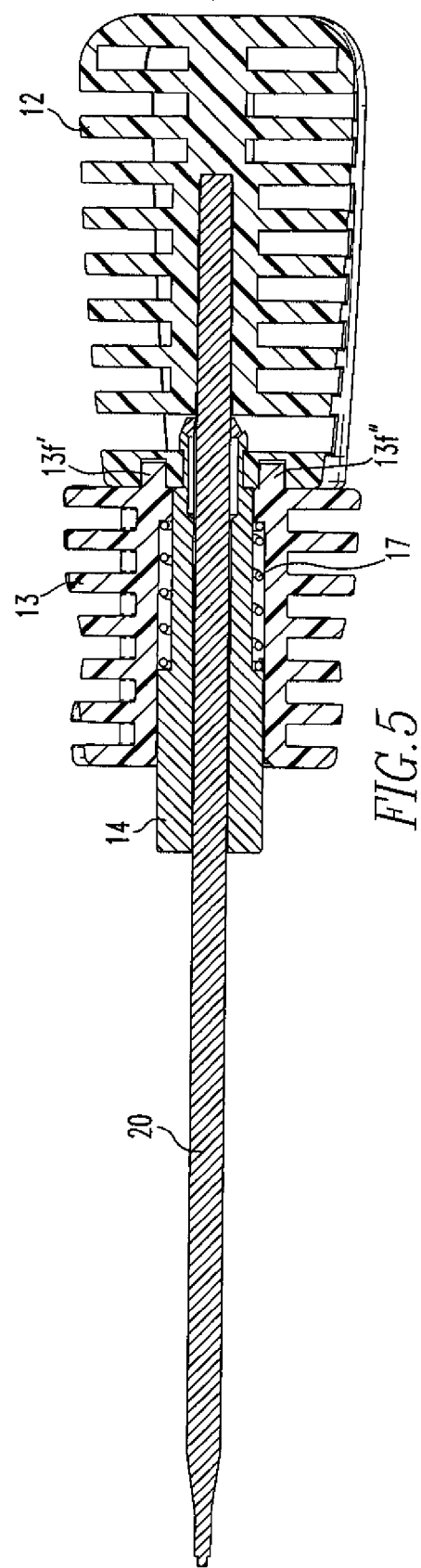
FIG. 5 shows a cross-sectional side view of the suture anchor inserter of FIG. 1.

The central component 13 includes a top surface 13a having a groove 13c, a bottom surface 13b having a groove 13d, a front portion 13e, a back portion 13f including two tabs (13f', 13f" FIG. 5), and a through hole 13g. The tabs 13f', 13f" are diagonally spaced from one another and, as shown in FIG. 5, are housed within one of the crevices 12d', 12d" of the slots 12d both before and after rotation of the central component 13, as will be further described below.

The distal component 14 includes a front portion 14a, a back portion 14b, and a through hole 14c. The front portion 14a includes suture retainers 14d and the back portion 14b includes prongs 14e with slots 14f located between the prongs 14e that extend a partial length of the back portion 14b. For the purposes of FIG. 2, only two suture retainers are shown. However, more than two suture retainers may be used. In addition, for the purposes of FIG. 2, only two prongs and one slot are shown. In practice, four prongs and four slots are used. However, any number of prongs and slots may be used. Each prong 14e includes a depression 15 that facilitates coupling of the distal component 14 to the proximal component 12, as will be further described below. A coil 17 is disposed on the back portion 14b to provide compression between the central component 13 and the O-rings 12e and provide pressure on suture extending between the proximal component 12 and the central component 13, as will be further described below.

The shaft 20 includes a distal end 20a configured for engagement with a suture anchor, a proximal end 20b coupled to the handle 11, and channels 20c extending a partial length of the shaft 20. For the purposes of FIG. 2 only one channel 20c is shown. In practice, two channels 20c are used. However, more than two channels 20c may be used. The suture retainers 14d are housed within the channels 20c and retain suture within the channels 20c prior to advancement of the suture anchor into bone, as will be further described below. The proximal end 20b is substantially round with a portion 20b' that is flat. As shown in FIG. 4, the opening 12c of the proximal component 12 also includes a flat portion 12c' for mating with the flat portion 20b' of the proximal end 20b. In addition, the proximal end 20b includes a knurled surface. The flat portion 20b' and the knurled surface provide for increased coupling of the shaft 20 to the proximal component 12, as will be further described below.

Figure 6:
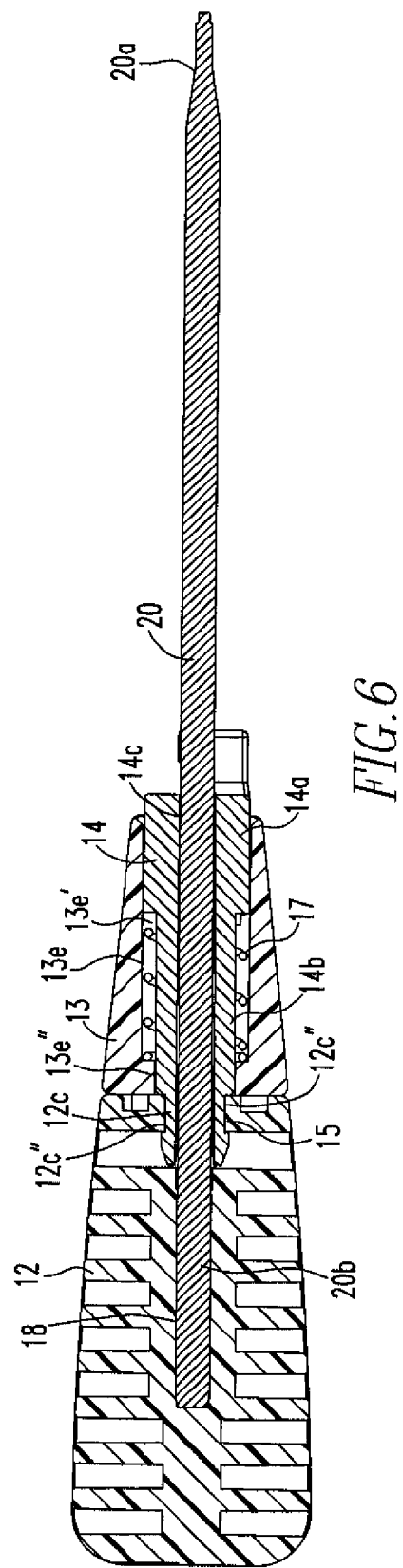
FIG. 6 shows another cross-sectional side view of the suture anchor inserter of FIG. 1.
Figure 7:
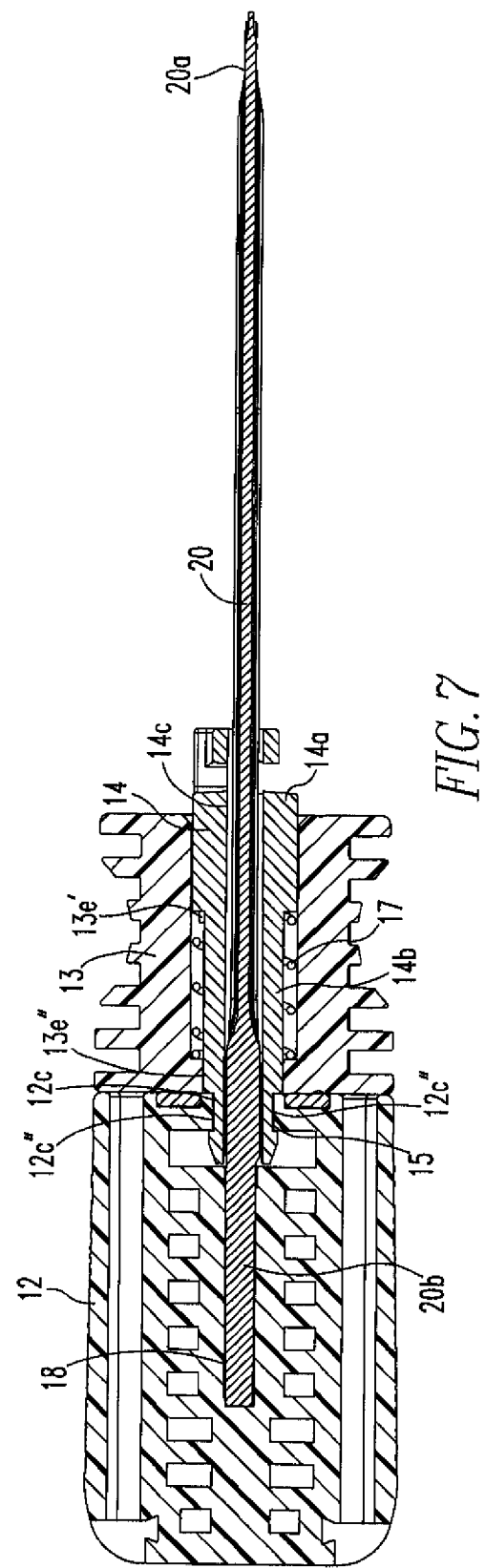
FIG. 7 shows a cross-sectional top view of the suture anchor inserter of FIG. 1.

As shown in FIGS. 6 and 7, the proximal component 12 includes an aperture 18, in addition to the opening 12c, and the through hole 13e of the central component 13 includes a first section 13e' and a second section 13e" having a smaller diameter than the first section 13e'. The distal component 14 is disposed within the opening 12c of the proximal component 12 and the through hole 13e of the central component 13 such that walls 12c" of the opening 12c are housed within the depression 15 and areas of the first and second sections 13e', 13e" engage the central component 13, respectively, so as to couple the distal component 14 to the proximal component 12 and the central component 13.

The coil 17 is disposed on the distal component 14 and is located within the first section 13e' of the through hole 13e between the distal component 14 and the central component 13. For the purposes of FIG. 6, the coil 17 is shown in a non-compressed state. However, in practice, the coil 17 will be in a compressed state such that the coil will be disposed only on the back portion 14b. The shaft 20 extends through the through hole 14c of the distal component 14 and the proximal end 20b is housed within the aperture 18 of the proximal component 12. As mentioned above, the knurled surface of the proximal end 20b provides for increased coupling between the proximal end 20b and the aperture 18 and, therefore, between the shaft 20 and the proximal component 12.

Figure 8:
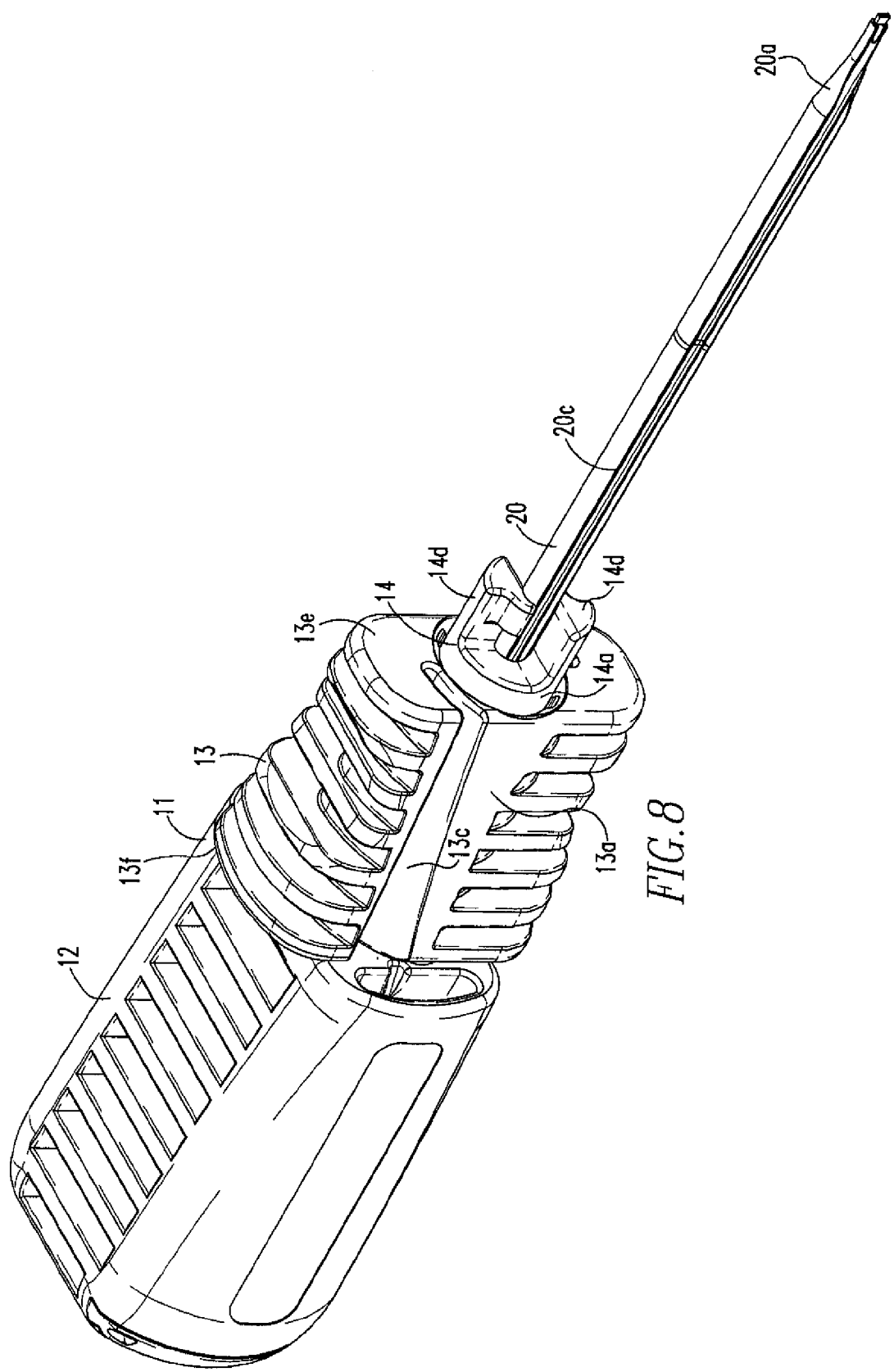
FIG. 8 shows a perspective view of the suture anchor inserter of FIG. 1 with the central component rotated relative to the proximal component.
Figure 9:
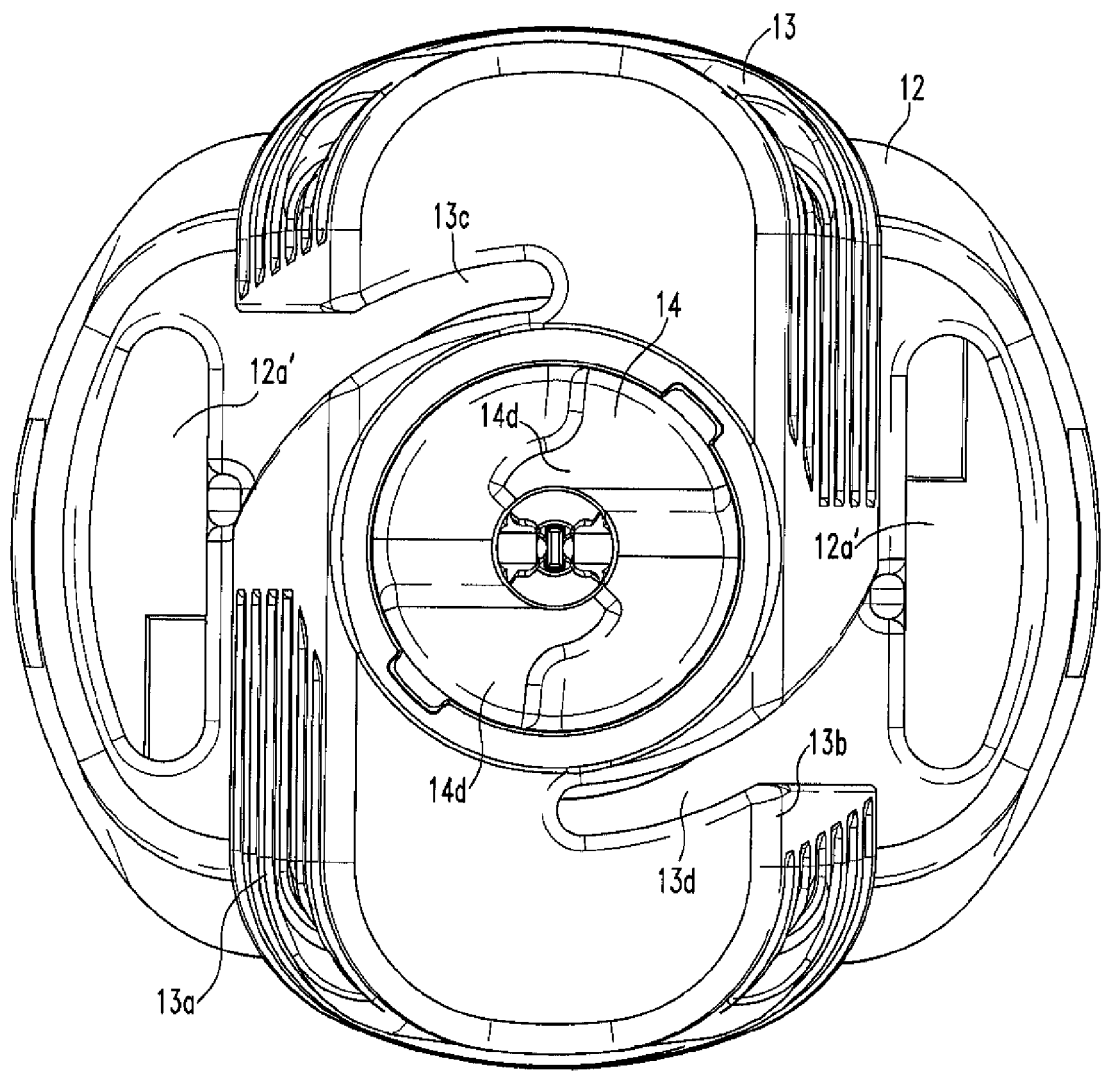
FIG. 9 shows a front view of the suture anchor inserter of FIG. 8.

As shown in FIGS. 8 and 9, the central component 13 has been rotated relative to the proximal component 12. For the purposes of this disclosure, the central component 13 is rotated at about a 90° angle relative to the proximal component 12, but other angles between about 0° and about 90° are also within the scope of this disclosure. As can be seen in FIGS. 8 and 9, rotation of the central component 13 allows for removal of the suture retainers 14d from the channels 20c and uncovering of the openings 12a' to the holes 12a, which, as will be further described below, will allow for removal of suture and needles from the channels 20c, the grooves 13c, 13d and the holes 12a.

Figure 10:
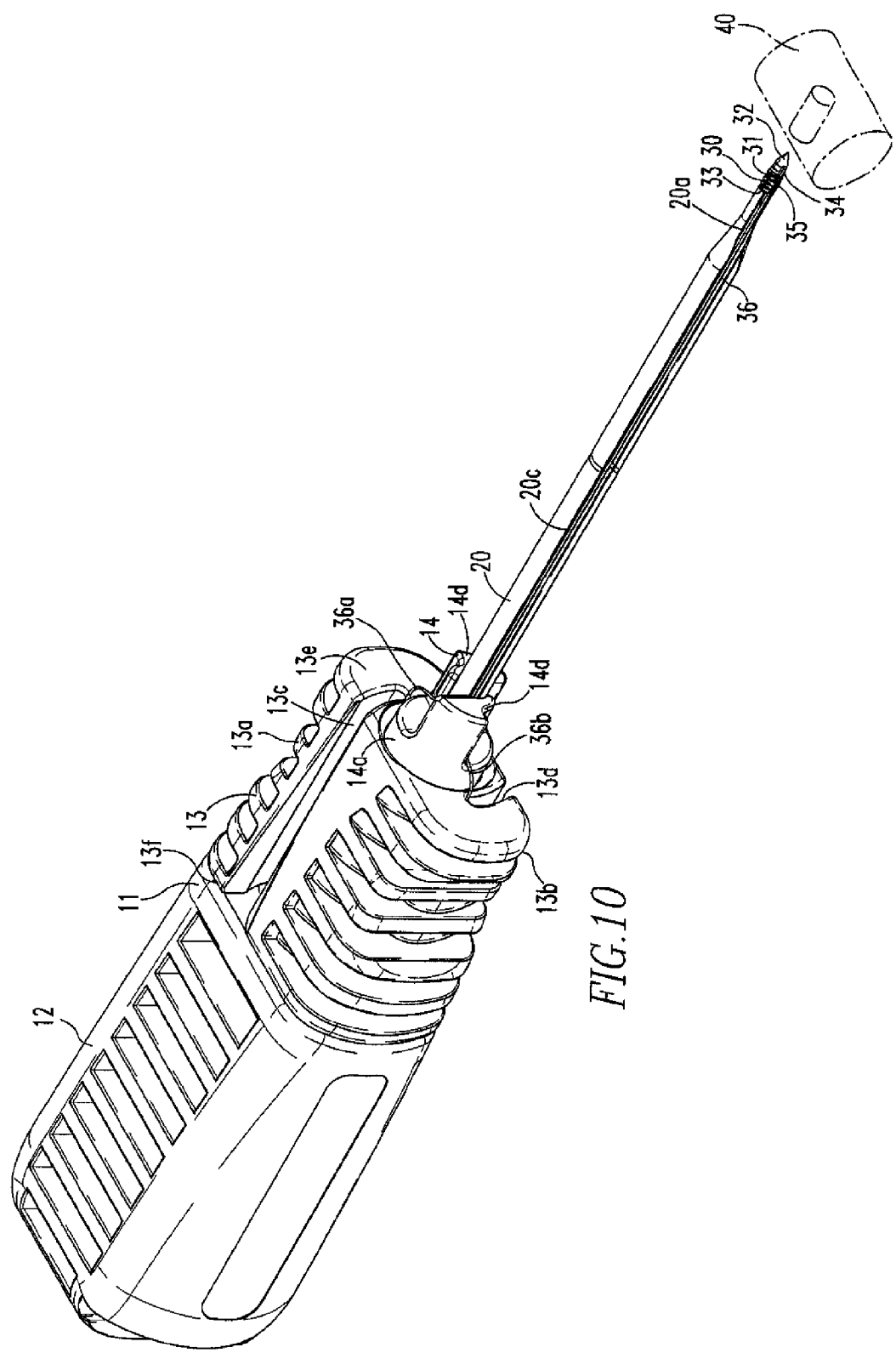
FIG. 10 shows the suture anchor inserter of FIG. 1 during insertion of an anchor into bone.

In FIG. 10, the inserter 10 is shown prior to advancement of an anchor 30 into bone 40. The anchor 30, which is coupled to the distal end 20a of the shaft 20, includes a body 31 having a distal portion 32, a proximal portion 33, and an outer surface 34 including threads 35. The threads 35 allow for rotary advancement of the anchor 30 into bone 40. However, surface features other than threads 35 may be located on the outer surface 34. For example, circumferentially extending ribs or barbs may located on the outer surface 34 to allow for axial advancement of the anchor 30 into bone 40. In addition, the outer surface 34 may include both threads and barbs for both rotary and axial advancement of the anchor 30 into the bone 40.

Figure 11:
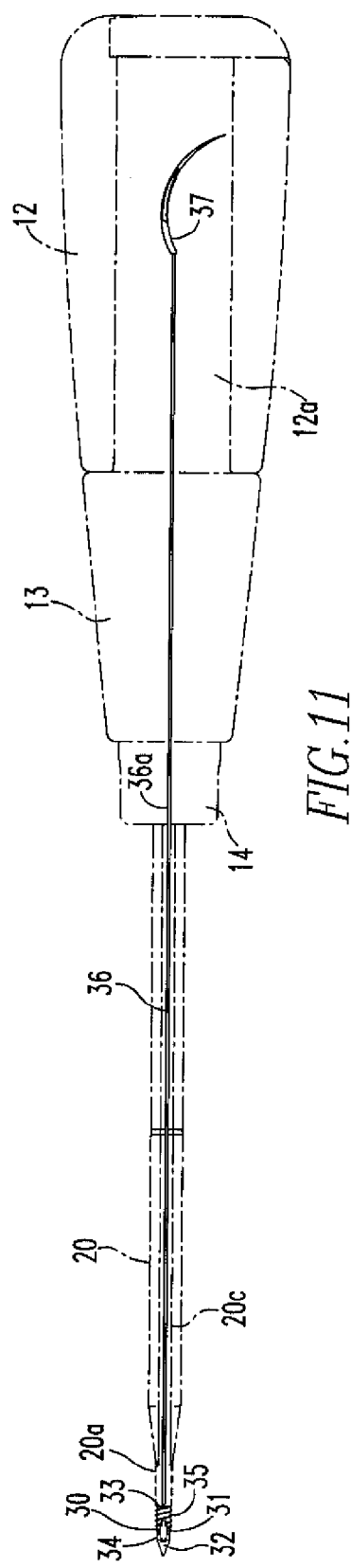
FIG. 11 shows a cross sectional view of the suture anchor inserter of FIG. 10.
Figure 12:
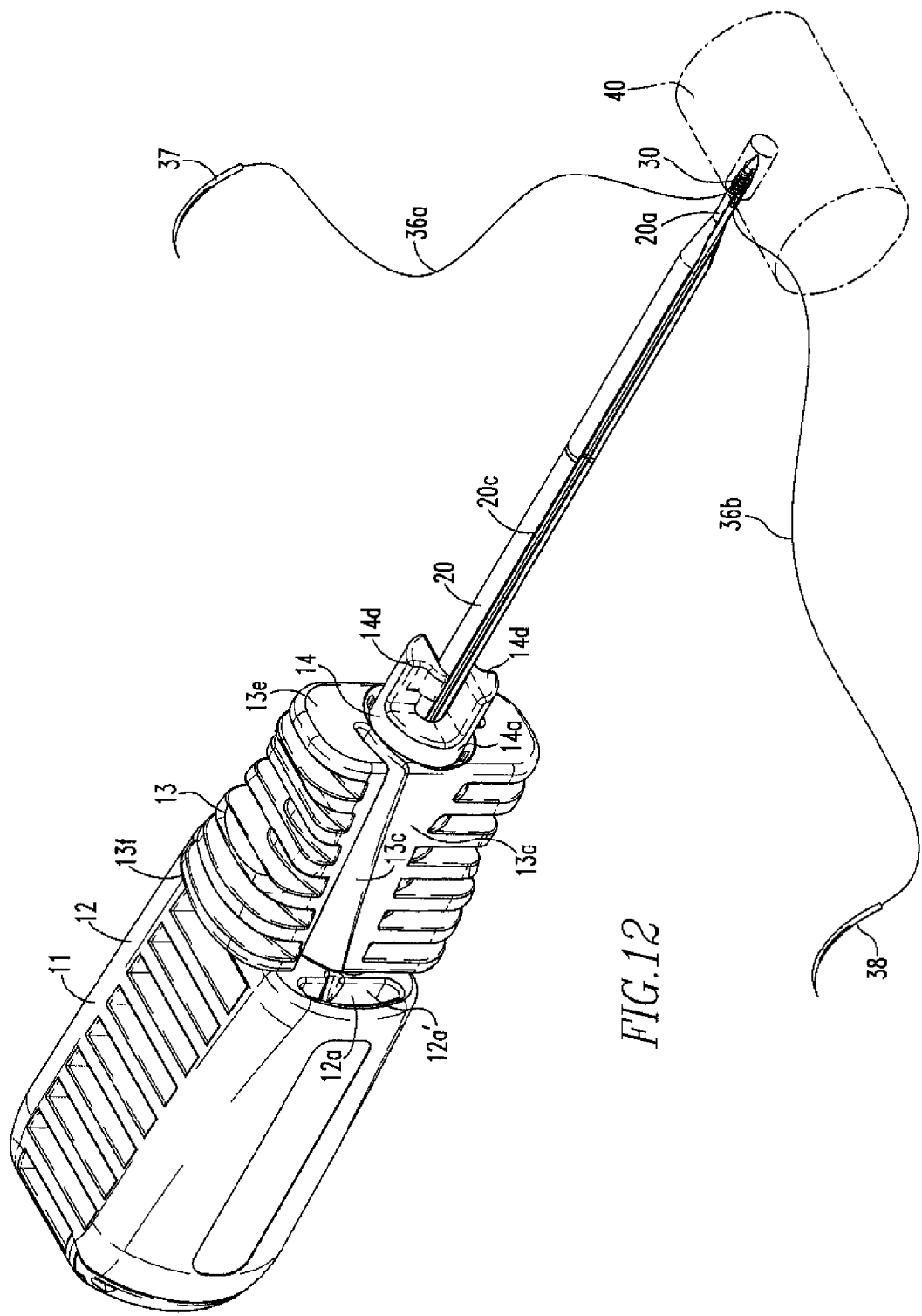
FIG. 12 shows the suture anchor inserter of FIG. 10 after insertion of the anchor into bone and rotation of the central component relative to the proximal component.
Figure 13:
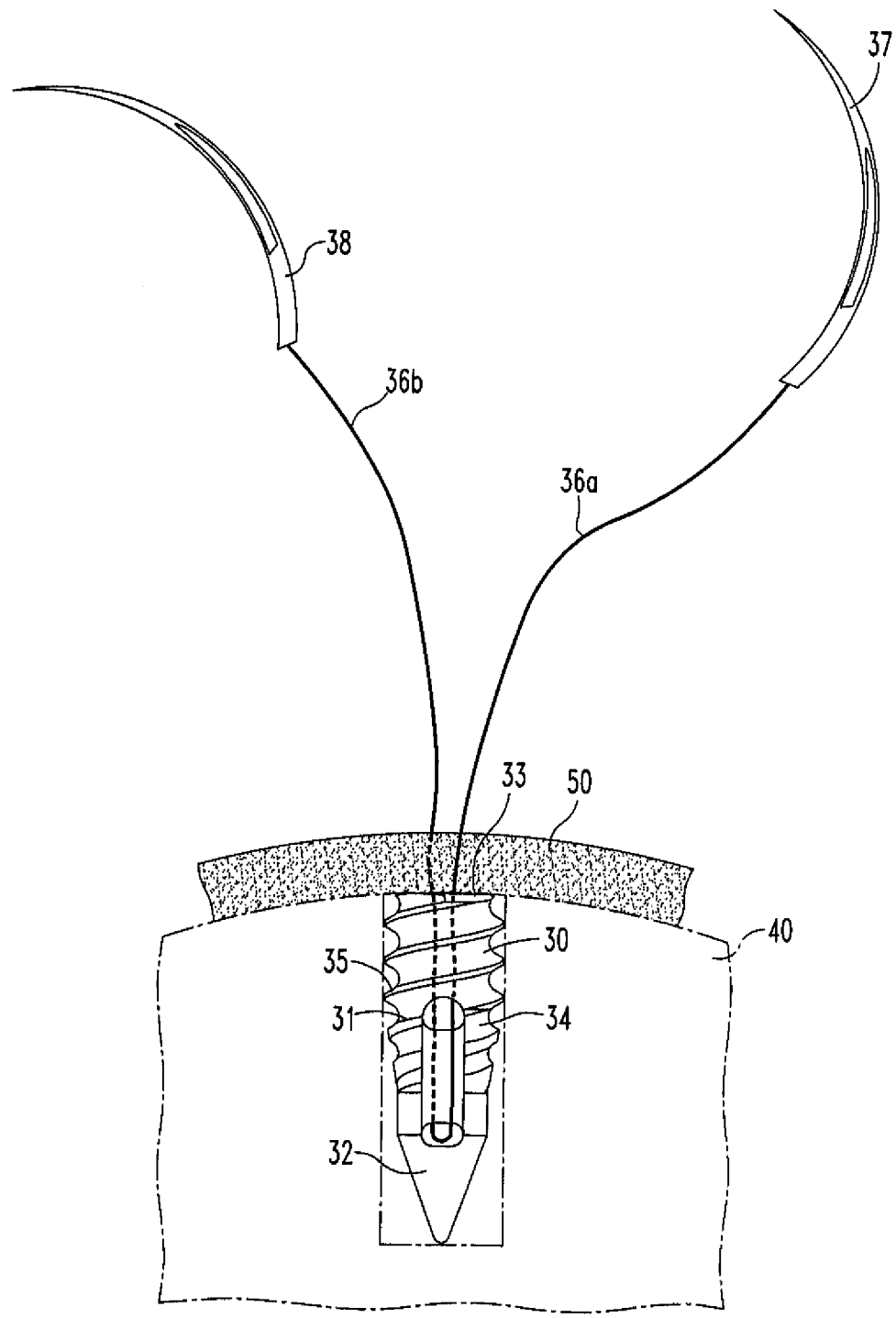
FIG. 13 shows a cross-sectional view after insertion of the anchor into bone and the suture and needles through soft tissue.

The anchor 30 also includes a suture 36 coupled to the anchor 30. The suture 36 includes two ends 36a,36b that extend from the proximal portion 33 of the anchor 30. As shown in FIGS. 11-13, needles 37,38 are coupled to the ends 36a,36b of the suture 36. The ends 36a,36b are housed within the channels 20c and extend through the grooves 13c,13d and into the holes 12a. As shown in FIG. 11, the needles 37,38 are housed within the holes 12a. The ends 36a,36b are retained within the channels 20c by the suture retainers 14d, as stated above. Similarly, as stated above, the ends 36a, 36b extend between the central component 13 and the proximal component 12. This interaction between the central component 13, the proximal component 12, and the ends 36a,36b allows for the ends 36a,36b to be retained in the grooves 13c,13d. Finally, the needles 37,38 are retained in the holes 12a due to the central component 13 covering the openings 12a' to the holes 12a. The tabs 13f', 13f" of the central component 13 are housed within the crevices 12d' prior to advancement of the anchor 30, thereby substantially reducing the possibility of rotation of the central component 13 during advancement of the anchor 30.

As shown in FIG. 12, after the anchor 30 is inserted into bone 40, the central component 13 is rotated relative to the proximal component 12 such that the tabs 13f', 13f" are removed from crevices 12d' and placed within crevices 12d". Upon rotation of the central component 13, the suture retainers 14d are removed from the channels 20c, the ends 36a,36b no longer extend between the central component 13 and the proximal component 12, and the central component 13 no longer covers the openings 12a' to the holes 12a. This allows the ends 36a,36b and the needles 37,38 to be disengaged from the inserter 10. After removal of the inserter 10, a soft tissue 50 is placed over the anchor 30 and the ends 36a,36b and needles 37,38 are passed through the soft tissue 50, as shown in FIG. 13. The ends 36a,36b and needles 37,38 are subsequently used to secure the tissue 50 to the bone 40 and close the surgical area.

The shaft 20 includes a stainless steel material, but may be made from any other metal or non-metal material that is bio-compatible and strong enough to withstand the forces that are placed on the shaft 20 during surgery. The shaft 20 may be machined, die drawn and subsequently machined, or made by any other method known to one of skill in the art. The shaft 20 is coupled to the handle 11 via a press-fit procedure. However, other methods of coupling the handle 11 to the shaft 16 are also within the scope of this disclosure. The components of the handle 11, except for the coil 16 and the o-rings 12e, are of a non-metal material, but may be made from a metal material, and are made via an injection molding process. However, other methods of making are also within the scope of this disclosure. The coil 16 is of a metal material and the o-rings 12e are made from silicon. However, the o-rings 12e may be made from another non-metal material, including, but not limited to, rubber.

The needles 37,38 are made from stainless steel and are coupled to the ends 36a,36b of the suture 36 via any method known to one of skill in the art. In addition, more than one suture/needle combination may be coupled to the anchor 30 and any suture known to one of skill in the art may be used. For the purposes of this disclosure, the anchor 30 is made from a non-metal, non-absorbable material. However, non-metal, absorbable materials or metal materials may be used. In addition, prior to advancement of the anchor 30 into bone 40, a hole may be made in the bone 40 for housing of the anchor 30.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A suture anchor inserter comprising:
a handle comprising:
a proximal component, a central component coupled to the proximal component, and a distal component coupled to the proximal component and the central component, the central component including a front portion, a back portion opposing the front portion, and a through hole extending, longitudinally, between the front and back portions, a portion of the distal component located within the through hole;
a shaft comprising a proximal end and a distal end, the proximal end coupled to the handle, wherein the central component is capable of rotating relative to the proximal component around a longitudinal axis passing through the handle and the shaft;
wherein the central component further comprises a top surface and a bottom surface each extending between the front and back portions of the central component, the top surface and the bottom surface both comprising a groove extending, longitudinally, between the front and back portions of the central component; and
wherein each groove includes a first opening and a second opening wider than the first opening.

2. The suture anchor inserter of claim 1 wherein the distal end of the shaft is configured to couple a suture anchor including a suture.

3. The suture anchor inserter of claim 2 wherein the grooves of the central component are configured to house legs of the suture.

4. The suture anchor inserter of claim 1 wherein the proximal component further comprises at least two holes.

5. The suture anchor inserter of claim 4 wherein the at least two holes are each configured to house a needle coupled to an end of a suture.

6. The suture anchor inserter of claim 1 wherein the distal component further comprises a front portion and a back portion, the front portion comprising at least two suture retainers.

7. The suture anchor inserter of claim 6 wherein the shaft further comprises at least two channels, each channel housing one of the at least two suture retainers.

8. The suture anchor inserter of claim 7 wherein the channels are configured to house the ends of the suture and the suture retainers are configured to retain the ends of the suture.

9. The suture anchor inserter of claim 1 wherein the proximal portion further comprises at least two slots with each slot having a first crevice and a second crevice.

10. The suture anchor inserter of claim 9 wherein the central component further comprises at least two tabs, the two tabs disposed within the first crevice of each slot.

11. A method of inserting a suture anchor into bone comprising:
providing a suture anchor inserter comprising a handle including a component capable of rotation relative to another component of the handle, a shaft coupled to the handle, and the suture anchor including a suture coupled to the shaft, wherein each of the components includes a top surface, a bottom surface, and sides narrower than the top and bottom surfaces, and extending between the top and bottom surface, and wherein the top and bottom surfaces of the component capable of rotation include grooves extending, longitudinally, between opposed ends of the rotatable component, each of the grooves including a first opening and a second opening wider than the first opening;
inserting the suture anchor into bone;
rotating the component relative to the other component of the handle, rotation of the component occurring around a longitudinal axis of the handle and the shaft such that when the component is rotated into a first position, the top and bottom surfaces of the component are aligned with the top and bottom surfaces of the other component, and when the component is rotated into a second position, the sides of the component are aligned with the top and bottom surfaces of the other component; and
removing the inserter.

12. The method of claim 11 wherein the suture comprises at least two ends, the ends comprising a needle coupled to each end, the needles housed within the handle.

13. The method of claim 12 wherein rotation of the component allows for release of the suture and the needles from the handle.

14. The method of claim 11 wherein the other component is located proximal to the rotatable component, the other component including at least two slots with each slot having a first crevice and a second crevice.

15. The method of claim 14 wherein the rotatable component further comprises at least two tabs, the two tabs disposed within the first crevice of each slot prior to rotation of the rotatable component and disposed within the second crevice of each slot after rotation of the rotatable component.

16. A suture anchor inserter comprising a handle including a proximal component, a central component coupled to the proximal component, and a distal component coupled to the proximal component and the central component, and a shaft coupled to the handle,
   wherein the central component is capable of rotating relative to the proximal component around a longitudinal axis passing through the handle and the shaft, the central component further comprises a groove extending, longitudinally, between opposed ends of the central component, the groove including a first opening and a second opening wider than the first opening; and
   wherein the proximal component includes a surface facing the central component, the surface having at least two holes.

17. The suture anchor inserter of claim 16 wherein the shaft is configured to couple to a suture anchor.

18. A suture anchor inserter comprising:
   a handle comprising:
      a proximal component, a central component coupled to the proximal component, and a distal component coupled to the proximal component and the central component, the central component including a through hole extending along a longitudinal axis of the central component, a portion of the distal component located within the through hole; a shaft comprising a proximal end and a distal end, the proximal end coupled to the handle, wherein the central component is capable of rotating relative to the proximal component around a longitudinal axis passing through the handle and the shaft;
   wherein the proximal component further comprises at least two holes each having an axis different than an axis of the through hole of the central component; and
   wherein the central component further comprises a groove extending, longitudinally, between opposed ends of the central component, the groove including a first opening and a second opening wider than the first opening.

19. A suture anchor inserter comprising:
   A handle comprising:
      a proximal component, a central component coupled to the proximal component, and a distal component coupled to the proximal component and the central component, the central component located between the proximal and the distal components;
   a shaft comprising a proximal end and a distal end, the proximal end coupled to the handle, wherein the central component is capable of rotating relative to the proximal component around a longitudinal axis passing through the handle and the shaft;
   wherein the proximal component includes a top surface, a bottom surface, and sides narrower than the top and bottom surfaces and extending between the top and bottom surfaces;
   wherein the central component includes a top surface, a bottom surface, and sides narrower than the top and bottom surfaces, and the sides extending between the top and bottom surfaces, such that when rotated into a first position, the top and bottom surfaces of the central component are aligned with the top and bottom surfaces of the proximal component and when rotated into a second position, the sides of the central component are aligned with the top and bottom surfaces of the proximal component; and
   wherein the central component further comprises a groove extending, longitudinally, between opposed ends of the central component, the groove including a first opening and a second opening wider than the first opening.

20. An assembly comprising:
   a suture anchor inserter of claim 1; and
   a suture anchor with a suture, the suture anchor coupled to the distal end of the shaft of the inserter.

21. The assembly of claim 20 wherein the shaft of the inserter includes at least two channels each housing a suture retainer; and
   wherein the suture includes at least two ends, each of which is housed within a respective one of the channels and retained therein by a respective one of the suture retainers.

22. The assembly of claim 20 wherein the proximal component of the inserter includes at least two holes; and
   wherein the suture includes at least two ends, each of which is coupled to a needle, and each needle is housed within one of the at least two holes.

23. The assembly of claim 20 wherein the suture includes at least two legs, the legs housed within the grooves of the central component of the inserter.

* * * * *